(12) United States Patent
Jelonek et al.

(10) Patent No.: US 7,035,702 B2
(45) Date of Patent: Apr. 25, 2006

(54) METHODS FOR DENTAL RESTORATION

(75) Inventors: Thomas Jelonek, Montreal (CA);
Pierre Breton, Montreal (CA);
Pierre-Jules Tremblay, Montreal (CA);
Peter Whaite, Montreal (CA)

(73) Assignee: Cynovad Inc., Ville Saint-Laurent (CA)

( * ) Notice: Subject to any disclaimer, the term of this patent is extended or adjusted under 35 U.S.C. 154(b) by 0 days.

(21) Appl. No.: 10/667,967

(22) Filed: Sep. 23, 2003

(65) Prior Publication Data

US 2004/0167646 A1   Aug. 26, 2004

Related U.S. Application Data

(63) Continuation of application No. PCT/IB02/02215, filed on Mar. 22, 2002.

(30) Foreign Application Priority Data

Mar. 23, 2001   (CA) .................................... 2342709

(51) Int. Cl.
*G06F 19/00*   (2006.01)
(52) U.S. Cl. ..................... 700/97; 700/104; 700/106; 700/118; 700/119; 703/2; 433/223
(58) Field of Classification Search ............... 433/223; 700/97, 104, 106, 118, 119
See application file for complete search history.

(56) References Cited

U.S. PATENT DOCUMENTS 4,742,464 A   5/1988   Duret et al.
6,008,905 A   12/1999  Tremblay et al.
6,093,019 A   7/2000   Goley et al.
6,786,726 B1 *  9/2004  Lehmann et al. ........... 433/223

FOREIGN PATENT DOCUMENTS

| EP | 0 824 897 A2 | 2/1998 |
| EP | 0 913 130 A | 8/1998 |
| FR | 2 744 012 | 8/1997 |
| NL | 1 007 059 | 1/1998 |
| WO | WO 98/448065 | 10/1998 |

OTHER PUBLICATIONS

Pierre et al., "Esthetic Option for the Implant-Supported Single-Tooth Restoration- Treatment Sequence With a Ceramic Abutment", Journal of the Canadian Dental Association, Oct. 2001, vol. 67 No. 9.*

* cited by examiner

*Primary Examiner*—Leo Picard
*Assistant Examiner*—Carlos Ortiz-Rodriguez
(74) *Attorney, Agent, or Firm*—Ogilvy Renault LLP

(57) ABSTRACT

The present invention provides a method for preparing dental restorations, the method comprising the steps of (a) compiling a database of materials for use in preparing a dental restoration; (b) compiling a database of procedures for preparing the dental restoration; (c) determining the geometrical constraints of the dental restoration; (d) determining the aesthetic constraints of the dental restoration; and (e) inputting the geometrical constraints and the aesthetic constraints to a computer to mathematically select from the material database and the procedure database a recipe for producing the dental restoration.

57 Claims, 2 Drawing Sheets

SCHEMATIC REPRESENTATION OF LIGHT / MATTER INTERACTION

METHODS FOR DENTAL RESTORATION

CROSS-REFERENCE TO RELATED APPLICATIONS

The present application is a continuation of PCT application PCT/IB02/02215 designating the United States having international filing date Mar. 22, 2002 and benefits from the priority of Canadian application 2,342,709.

FIELD OF THE INVENTION

The present invention relates to dentistry. More specifically, the present invention is concerned with dental restoration and prosthesis.

BACKGROUND OF THE PRESENT INVENTION

The measurement of objects and use of the measurements to manufacture replacement parts substantially identical to the original object has long been a goal of industry. In the field of dentistry and the methods of making dental prostheses, e.g., crowns, plates and replacement teeth, this has especially been the case. In the early prior art, the methods required a multiplicity of steps, many of which required intervention in the mouth of the patient. Not only was the patient required to attend the dental practitioner a relatively large number of times, but also the intervention frequently was painful, especially during the fitting stages.

For example, in forming a dental crown, the operations included the grinding of the tooth to be replaced in order to obtain a truncated stump, the taking of an impression of the stump using an elastomer in order to obtain a mold whose hollow part had a shape that was complementary to that of the stump, the casting of plaster into the mold in order to obtain a reproduction of the stump, the preparation of the crown in wax taking into consideration adjacent and antagonistic teeth (a process that was generally highly subjective and the effect of which required high skill and long years of experience by the practitioner), the positioning of the crown in a coating cylinder, the melting out of the wax, the injection of molten metal to replace the wax, the stripping and polishing of the metal crown, and, the setting of the crown on the stump.

in spite of the fact that these numerous operations were carried out by highly skilled dental practitioners, in many cases the prosthesis was then required to be further modified after the initial formation. Because of the large number of steps that were involved, and the fact that even with mechanical impressions accurate fits could not be ensured, and because the relationship of each prosthesis to the adjacent and antagonistic teeth had to be gauged subjectively by the practitioner, the production of a dental prosthesis rarely could be accomplished without many visits to the practitioner for further modifications. Moreover, despite the numerous fitting visits and modifications, the danger that the finished prosthesis would cause discomfort to the patient remained.

Other disadvantages of the early dental prosthesis methods included the use of metals as the material for many dental prostheses. For example, the metals used had to be fluid or malleable at easily obtainable temperatures. The numerous steps in preparing and fitting prostheses required the intervention of a laboratory and skilled practitioners at different stages in addition to a dental surgeon. The equipment, including an oven, sand-blasting machine, and inserting equipment, contributed significantly to the cost of producing the prostheses.

Dental material manufacturers often also provide guidance to use their different products to achieve dental restorations of a given appearance. However, this guidance is often limited to theoretical cases with a prescribed appearance matching a finite number of shade guide tabs. The main problem is that natural teeth never perfectly match the shade tabs and translucency is not usually taken into account.

Furthermore, the recipes provided assume that there is a given constant thickness available to layer the different dental material to achieve the desired result. The problem is that this is often not the case.

The basic laws of physics modeling the interaction of light with matter, including the diffusion of light in translucent material, are well known and documented in the literature. In particular, the Kubelka-Munk model has already been suggested for the use of uniformly layered porcelain. One of the key challenges, however, is the inverse problem; that is given a desired appearance for teeth, how can one recreate it.

Another problem existing in the prior art is in the currently commercially available cosmetic software packages that use images of smiling faces as input and modify these images with standard photo manipulation tools. The dentists use before and after images to sell dental procedures to patients. There is unfortunately no correspondence between software tools and the dental procedures available. The dental procedures may yield results that are not satisfactory to the patient because of the representations the dentist made with the cosmetic software.

Also, whereas U.S. Pat. Nos. 4,611,288, 4,663,720, 4,742,464, 4,952,149, 5,092,022 and 5,237,998 describe devices and methods that measure the shape of teeth and realize dental prosthesis, it is preferable to acquire more information to achieve aesthetic prosthesis. The information needed to achieve improved aesthetic prostheses is the appearance of the desired prosthesis.

An aesthetic smile is based on notion of morphology, symmetry, matched color and translucency, and natural look. There exist various commercially available cosmetic software packages that provide means to modify the shape and alter the color of the teeth. However, no known software is based on precise quantitative data on shape and appearance. The use of finite element analysis and computer simulation in prior art dentistry application is limited to mechanical property concerns.

SUMMARY OF THE INVENTION

It is an object of the present invention to provide a method to model teeth, prosthesis and dental material, a Computer Assisted Design (CAJ)) system and a database for the different families of teeth and/or prosthesis.

It is also an object of the present invention to provide a method to design dental restorations with predetermined aesthetic qualities.

It is another object of the present invention to provide a method for realizing aesthetic prosthesis.

It is a further object of the present invention to provide a method of communicating information related to dentistry and prosthesis.

In accordance with a first broad aspect of the present invention, there is provided a method for preparing dental restorations, the method comprising the steps of: (a) compiling a database of materials for use in preparing a dental restoration; (b) compiling a database of procedures for preparing the dental restoration; (c) determining the geometrical constraints of the dental restoration; (d) determining the aesthetic constraints of the dental restoration; and (e) inputting the geometrical constraints and the aesthetic constraints to a computer to mathematically select from the material database and the procedure database a recipe for producing the dental restoration.

In accordance with a second broad aspect of the present invention, there is provided method for designing dental restoration with predetermined aesthetic qualities, the method comprising: (a) compiling a database of criteria for use in designing an aesthetic dental restoration; (b) compiling a database of procedures for preparing the dental restoration; (c) determining the geometrical constraints of the dental restoration; (d) determining the aesthetic constraints of the dental restoration; and (e) inputting the geometrical constraints and the aesthetic constraints to a computer to mathematically select from the criteria database and the procedure database a feasible design for the dental restoration.

In accordance with a third broad aspect of the present invention, there is provided a method for producing an aesthetic prosthesis, the method comprising: (a) acquiring quantitative data on shape and appearance; (b) processing the quantitative data to determine the desired result; (c) further processing the quantitative data and the desired result to determine a method for achieving the desired result; (d) manufacturing the underlying structure of the prosthesis; and (e) finalizing the prosthetic work.

In accordance with a fourth broad aspect of the present invention, there is provided a method for communicating information related to dentistry comprising: (a) collecting information regarding a dentistry procedure; (1) communicating the information to a central source via a computer network for analysis.

DETAILED DESCRIPTION OF THE PRESENT INVENTION

Figure 1:
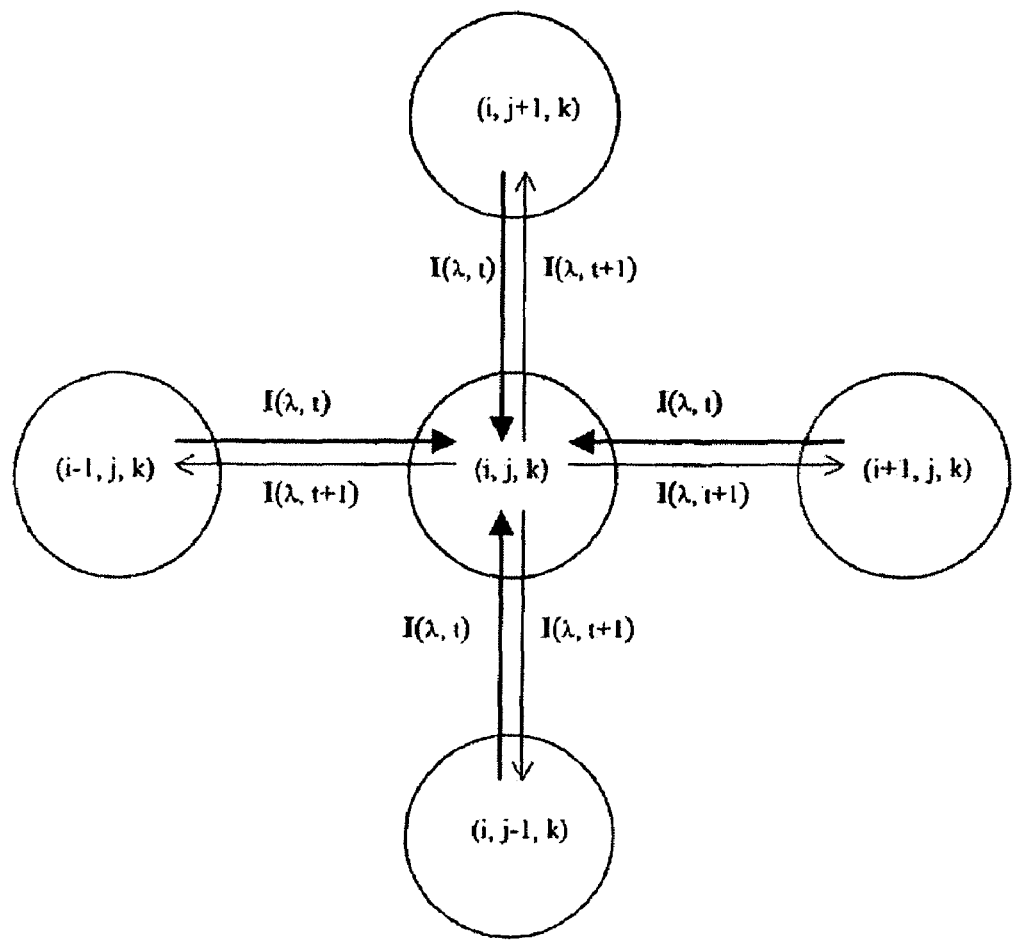
FIG. 1 depicts a schematic representation of voxels.

According to one aspect of the present invention there is provided a method to model teeth, prosthesis and dental material, a Computer Aided Design (CAD) system and a database for the different families of teeth and/or prosthesis.

Fixed prostheses are typically built in layers: the main layers are the sub-structure, the dentin and the enamel. Porcelain fused on metal (PFM) are a common type of prosthesis.

The sub-structure is made of metals (precious alloys, titanium, etc.) and the dentin and enamel layers are made of porcelain. With the advances in material sciences, more and more new materials are being used. For example, sub-structures are now sometimes made with pressed ceramic, zirconium oxide and lithium disilicate to improve the quality of the restoration.

The database and CAD system provide the geometrical data that constrain the finishing step in the fabrication of dental prosthesis, such as the thickness of the porcelain layer. The geometrical constraints to build the prostheses are either taken from a theoretical teeth library where standard preparations are identified, or they may be taken directly from the CAD system. French Patent No. 95-07795 describes one suitable method, which is implemented by Cynovad Inc. in their Pro 50 CAD software to provide such data and such theoretical teeth library.

The final prosthetic work, which is usually done by a dental technician, also has inherent constraints that must be taken into account in providing recipes to achieve a desired appearance.

The interaction of light with the teeth, prosthesis and dental materials is advantageously modeled based on known physical laws and measurements of material properties such as, but not limited to, absorption, transmittance, diffusion, reflection and refraction. Several sets of equations have been proposed to model the interaction of light with pigments contained in matter, such as, Beer's law, Kubelka-Munk, Saunderson etc. Such models are described in books such as Judd and Wyszecki, "Color in Business, Science and Industry," $3^{rd}$ edition; Lewis ed., "Pigment Handbook," 1988; Billmeyer and Salzman, "Principles in Color Technology," 1981; Hunter and Harold, ed., "The Measurement of Appearance", $2^{nd}$ ed., 1987; and in articles, such as, Vargas and Niklasson, "Applicability Conditions of Kubelka-Munk Theory," Applied Optic, 1997; and Hellmold et al., "Some Optical Properties of Enamel," Journal of Non-Crystalline Solids, 1991.

Several numerical techniques are blown to resolve such set of equations for complex three-dimensional geometries, for example, finite elements method, finite differences method, finite volume method, computer modeling and simulation methods, etc. These methods are described in books such as Bauer, ed., "What Every Engineer Should Know About Finite Element Analysis," 1988; Ingels, "What Every Engineer Should Kow About Computer Modeling and Simulation;" Tuma, "Handbook of Numerical Calculations in Engineering;" and in articles such as Langer et al., "Massively Parallel Radiosity in the Presence of Multiple Isotropic Volume Scattering," Graphics Interface '95 proceedings, 1995. Some representative finite element software packages that are commercially available are: ABAQUS, ANSYS, AOS/MAGNETIC, FIDAP, MARC, NASTRAN, PDA/PATRAN, STARDYNE, STRUDL, SUPERTAB.

The method uses the desired appearance as input; the system assumes standard shape constraints. The standard shape constraints for each family of teeth are provided in a theoretical tooth library, such as the one that comes with the Cynovad Pro 50™ CAD software. The standard shape constraints are based on the tooth number and the appropriate tooth family. The tooth number identifies the position of the tooth in the dental arcade, whether it is a molar, premolar, canine or incisor. Dental practitioners can customize teeth families at will. Typically, teeth families are differentiated according to the different age group of the patient.

The method can also use the shape constraints provided by a CAD system as input. Thus, alternatively, the shape can be directly provided by the CAD system. Such CAD systems use a shape-measuring device such as an optical sensor (e.g., Cynovad Pro 50™ system) or a tactile system (e.g., Nobel Biocare Procera™ system). Using the CAD software, the dental practitioner defines the shape of the prostheses. This task could simply involve adjusting the size and form of the selected theoretical tooth to ensure a perfect fit, or require extensive design for a patient that has an abnormal dental arcade.

The method provides as a result a recipe that is consistent with the art of reproducing the desired appearance. The initial constraints from the dentists and dental technicians are identified limiting the choice of material and complexity of the work. The knowledge-based system identifies the most common procedures to achieve a prosthesis with the desired morphology and the desired appearance considering the given constraints. Such procedures are defined parametrically: typically, the prosthesis is built layer-by-layer enveloping the tooth stump to build a prosthesis with the desired morphology. Each layer is characterized by its shape, $L(s,t)$, its thickness $(T(s,t)$, and its material compositions, $M(s,t)$. The procedure constrains the variation of these parameters, for example, by qualifying the tapering layer or limiting the minimal size of regions of different material composition. The appearance resulting from a procedure given a set of parameters is calculated with the light-prosthesis interaction model. The recipe is then obtained by selecting the set of parameter that best approach the desired appearance by standard numerical optimization techniques.

For example, the recipe will state that given a substructure made of a given material, an opaque layer of a given masking paint must first be applied then different given porcelain dentin, dentin and enamel powders should be layered according to a given mapping and fired with a given firing sequence and instructions.

In a preferred embodiment of the method, the system operates by dividing the prosthesis volume into a large number of voxels (small volume elements) defining a mesh that reflects the layered structured of the prosthesis and teeth. For each voxel, the light rays of different wavelengths entering the voxel from neighboring voxels are absorbed, diffused, reflected, refracted and transmitted to neighboring voxels according to the material properties of the material employed in this voxel. Each voxel is thus parameterized with absorption, diffusion, reflectance, refraction and transmittance coefficients that are dependent on the wavelength of the light entering the voxel. Given some known illumination, the reflected light can be calculated numerically.

Figure 2:
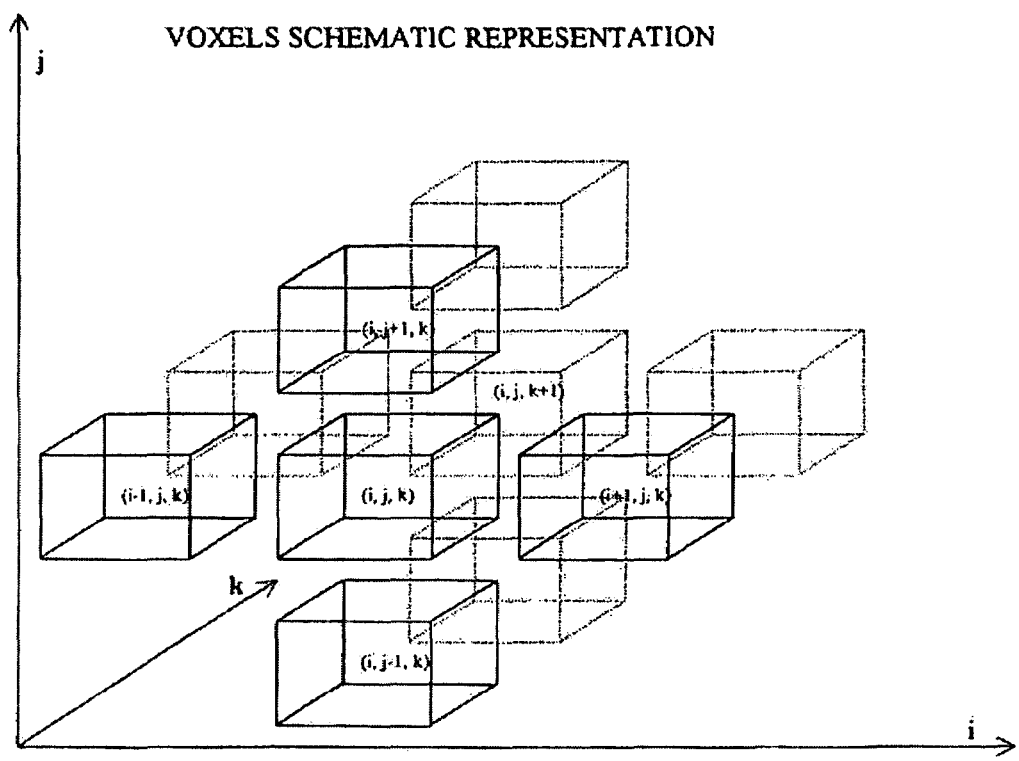
FIG. 2 depicts a schematic representation of light/matter interaction.

Referring to FIGS. 1 and 2, at time t, a light ray $I^{(1,0,0)}(\lambda, t)$ enter a given voxel $(i, j, k)$ from the neighboring voxel $(i+1, j, k)$. The ray is partly reflected $I^{(1,0,0)}(\lambda, t+1)$, partly transmitted $I^{(-0,0,1)}(\lambda, t+1)$, and partly diffused $I^{(0,1,0)}(\lambda, t+1)$, $I^{(0,-1,0)}(\lambda, t+1)$, $I^{(0,0,1)}(\lambda, t+1)$, $I^{(0,0,-1)}(\lambda,t+1)$, and partly absorbed. The overall light distribution is given by $I(\lambda, t+1)=M(\lambda) I(\lambda, t)$ where $M(\lambda)$ characterizes the optical properties of dental material and dental material interface, a function of wavelength $\lambda$.

The model does not necessarily need all of the parameters, often, the absorption and diffusion coefficients are the determining factors. The reflectance is useful to model the interface between layers of different materials. Other material properties such as opalescence, or fluorescence, could be added to this model, but are not important for most cases.

Given that it is humans who evaluate the appearance of teeth and dental prostheses, the model of the human visual system is used to reduce the complexity of the model calculation by considering the perception of colors, instead of the full range of wavelengths. The reflected light rays of differing wavelengths are weighted according to the CIE (Commission International de l'Éclairage) standard observer and integrated to generate the red, green and blue stimuli corresponding to human vision. A description of the model of the human visual system can be found in literature, such as in Healey et al., "Physics-based Vision, Principle and Practice-Color," 1992; and Hunt, "A Model of Colour Vision For Predicting Colour Appearance in Various Viewing Conditions," COLOR research and application, 1987.

To predict the reflected light, a number of different wavelengths representative of the human visible spectrum are used in combination with hypotheses of material properties to simplify the complexity of the calculations. For dental materials currently used commercially, often, red, green and blue wavelengths are sufficient. Incorporation of far red, yellow, cyan and violet improve the prediction. Further wavelengths should be considered based on the specific materials used to build the prosthesis. Better knowledge of material properties allows one to reduce the need of using large number of different wavelengths to model the light-matter interaction, especially with materials for which smooth extrapolation and interpolation are valid.

In a preferred embodiment of the method, the empirical knowledge of the expert dental technician for reproducing the desired appearance is stored and used to constrain the solution space both in terms of starting point and in terms of physical limitation of the dental technician ability to follow a given recipe.

In a preferred embodiment of the method of the present invention, in order to validate the method and to continuously refine the model to include a greater diversity of dental materials, a series of experiments is conducted consisting of fabricating prostheses according to recipes and measuring their appearance with Cynovad's ShadeScan System™ described in U.S. Pat. No. 6,008,905. For example, first one measures the appearance of simple blocks of uniform dental materials of different thickness, with different backgrounds; then layered blocks with different optical properties; layers with a simple distribution of different dental materials. By verifying the predictions of the appearance within a given precision desired one can validate the model.

However, whereas the model holds for simple configurations, increased quality requirements for more complex layering might require refining the model to account for effects not previously noticed or a better characterization of the dental materials. An example of a refinement of the model would be an increase in the number of neighbors (even more distant neighbors), hence considering a larger set of discretized. light ray vectors. Conducting a larger quantity of experiments with different users allows for the statistical validation of the recipes difficulty level. Such refinement may lead to different recipe strategy depending n the observed skills of a given dental technician.

Illumination consists of two parallel light beams at plus and minus 45 degrees from axis of measurement, which should be roughly perpendicular to the tooth or prosthesis surface. The illumination is constant within the volume id which the tooth or prosthesis should be positioned. The sensor is a calibrated color camera that provides accurate measurements of both the color and translucency of the tooth or prostheses.

The method is advantageously a knowledge-based system that includes: the art of reproducing the desired appearance as described by one or more expert dental technicians; a basic model of interaction of light with the teeth, prosthesis and dental materials along with specification of dental material properties; the cumulative data of experiments consisting of fabricating prosthesis according, for example, to a given recipe and measuring their appearance.

Knowledge-based systems are described in books such as, Ullman, "Principles of Database and Knowledge-base Systems," 1988; Tzafestas, "Knowledge-based System Diagnosis, Supervision, and Control," 1989; Schreiber, "KADS: A Principled Approach to Knowledge-Based System Development," 1993; and articles such as, Pierre et al., "A Knowledge-based System with Learning for Computer Communication Network Design," Telematics and informatics, 1990.

In a preferred embodiment, the recipes provided are layered distribution maps of materials of a-given thickness, including but not limited to, the substructure, opaque mask (optional), the dentin, the modifier stain (optional) and the enamel. The material and thickness of each layer is specified for each point of the distribution map. The layers may be subdivided into several sublayers, e.g., the dentin layer may be subdivided into an opaque dentin layer and a translucent dentin layer. A user-interface allows one to further constrain the solution space by limiting the choice of materials to those available to or preferred by the user and sets the coarseness of the recipe by defining the size of voxels in the distribution maps as well as limiting the number of sublayers.

The previous method can then be used to serve as input to a machine that automatically places the selected dental material at a given position to build prosthesis. The art of reproducing the desired appearance is made to also encompass the machine capacity and constraints.

The previous method can also serve to select and position a block of a given dental material for a milling machine, such as the PRO 50™ system from CYNOVAD™, producing prosthesis and/or substructures. The block of given material may be selected from sets of blocks of different dental materials of uniform appearance and/or of varying color and/or translucency.

Such a machine could be made for example with the plasma fusion of chosen dental material and projected on the prosthesis' substructures and/or molds. In a preferred embodiment, the machine is one that uses the same positioning technology as a milling machine and deposits layers of material with syringes, each syringe containing a different dental material. Other technologies, such as rapid-prototyping technologies, can also be used without departing from the spirit of the present invention.

According to another aspect of the present invention, there is provided a method to design dental restorations with predetermined aesthetic qualities.

To achieve high quality restorations, the method according to the second aspect of the present invention concerns cosmetic software that emulates dental procedures and predicts most likely outcomes and standard deviations based on precise quantitative measurements on the teeth's appearance, two-dimensional shapes and preferably also their three-dimensional shapes. Existing cosmetic software packages (e.g., ViperSoft) shows, by image processing, how a person's smile could look if certain changes were made to it. Whereas such cosmetic software packages do have an impact on the sales and marketing of dental procedures by providing before and after pictures, dental practitioners are often confronted with an impossible task of achieving the desired result.

By simulating the dental procedure, the present invention defines the morphological constraints. This procedure defines a new object that is partly tooth and partly prosthetic.

The model of light interaction with dental material is used predict the appearance of the dental procedure.

The cosmetic software uses models of the different dental procedures and accounts for their respective constraints, both mechanical and optical. A probabilistic model may also be used for procedures involving uncertainties with respect to their outcome.

The computer-aided design of prosthesis will involve endeavoring a harmonious match with adjacent teeth; propose if appropriate morphology and symmetry with respect to the central axis, interpolate between colors of neighboring teeth, and match the translucency pattern.

The models of the different dental procedures are evolved from the basic models of teeth, prosthesis and dental materials. The actual clinical dental procedures are monitored with before and after quantitative measurements of shape and/or appearance. To build a reliable database, this is preferably done at many different beta sites with numerous patients. When appropriate, these measurements are also made during procedures or after some time after the procedures. The range of possibility is thus defined. The knowledge-based system also evolves with the addition of new dental procedures and/or of new dental materials and/or of an expanded knowledge base of experiments.

For example, in tooth whitening with a given company's product applied according to specification, the appearance and the shape of the tooth is measured before and after each application, and subsequently at each visit by the patient.

According to a third aspect of the present invention, there is provided a method to realize aesthetic prosthesis. Generally the method comprises the following steps: acquiring quantitative data on both shape and appearance; processing this information to determine the desired result; filter processing this information to design how to achieve the desired result; manufacturing the underlying structure of the tools required to prepare the underlying structure if needed; and finalizing the prosthetic work.

Each of these steps will now be described in more detail. In Step 1, quantitative data on both shape and appearance are advantageously acquired by;

1. Combining the digital measurements of the appearance of the teeth, such as those obtained by devices and methods described in U.S. Pat. No. 6,008,905, and the digital measurements of the shape of teeth, such as those obtained by devices and methods described in U.S. Pat. Nos. 4,611,288, 4,663,720, 4,742,464, 4,952,149, 5,092,022 and 5,237,998. It is to be noted that other devices may also be used without departing from the spirit and nature of the present invention. The above-mentioned patents are hereby incorporated by reference in their entirety.

2. Communicating this information through Internet, or another network, to a design center node. The information can be transferred by any other means digital data are usually transferred, such as, but not limited to, direct modem line, solid-state, optical and/or magnetic devices such as diskettes, CD-ROM, DVD, Zip drive and/or flash card. The information on appearance and shape can be acquired by different individuals and sent separately to the cosmetic center node (e.g., dentist acquire and communicate digital data on the appearance; dental technician acquire aid communicate digital data on the shape).

In Step 2, the processing of this information to determine the desired result may be achieved by: an expert (typically a dental practitioner having years of experience in assessing what morphology is best in a given clinical situation and what aesthetic criteria to apply to propose a visually pleasing solution) or alternatively a knowledge-based system, using computer-aided design tools define the best shape and appearance for the prosthesis. Whereas the computer-aided manufacturing requires 3D shape data, the design can be limited to appearance and 2d shape data if fabrication is done with the traditional artisan techniques. Furthermore, the task of designing the desired morphology and/or shape and the task of designing the desired appearance can be done separately. However, it is preferable that the shape and appearance design be done in a coordinated fashion to take into account constraints due to the available dental material;

and communicating this desired result to a calculation center node. For example, if the objective set is to have a ceramic anatomical coping, the selected manufacturing process may be milling machines. The calculation center node would be selecting the color of the coping material and compute the trajectories of the cutting tools to fabricate the dental object.

The processing of this information to design how to achieve the desired result (step 3) is advantageously achieved by: an expert (one having a good understanding of the constraints related to a given manufacturing process and can deal with exceptions), or alternatively a knowledge-based system, using computer-aided manufacturing tools to define the best process to manufacture the prosthesis and/or the underlying structure and/or finishing requirements; and communicating the manufacturing process instructions to a production center node.

In step 4, manufacturing the underlying structure or the tools required to prepare the underlying structure is advantageously achieved by: people and machine executing said manufacturing process instructions. Manufacturing processes can be, but are not limited to, machine milling and/or rapid prototyping and/or deposition on model; and Communicating the finishing process instructions to a dental laboratory node.

In step 5, the prosthetic work is finalized by advantageously: people and machine executing said finishing processing instructions. Finishing processes can be, but are not limited to, polishing and etching substructures, masking, laying porcelains, ceramics, resins and/or composites dental material and/or firing, hardening.

A method that consists of the following steps allows one to outsource tasks to achieve aesthetic dental prosthesis:
1. Dentists initiating dental procedures that require the restoration or cosmetic alteration of the teeth;
2. Design centers processing the shape and/or appearance information to determine the desired result;
3. Calculation centers processing this information to design how to achieve the desired result;
4. Manufacturing centers executing instruction to produce the underlying structure if need;
5. Dental laboratory centers finalizing prosthetic work; and
6. Dentists completing dental procedures.

Each of these general steps Will now be described in further detail. In step 1, a dentist: makes imprints of a patient's teeth; or uses sensors to acquire digital shape information of a patient's teeth directly in patient's mouth; or makes imprints of patient's teeth and models to register the shape of teeth; or uses sensors to acquire digital shape information of patient's teeth from imprints and/or models; and/or uses sensors to acquire digital appearance information of patient's teeth directly in patient's mouth.

Dentists communicate digital information of appearance and/or shape information acquired from the above steps through Internet or modem line or other means of transmitting digital data to design centers along with complementary information to document cases and/or for transactional need. If needed, dentists send imprints or models to design centers. Exemplary of information to document the cases includes, but is not limited to the tooth number, the clinical condition and the dentist preferences to address the condition, and the client's personal preferences, such as, but not limited to, use of a more expensive full-ceramic crown providing better aesthetics versus a less expensive porcelain-fused-on-metal crown. Also, transactional information such as name, address, phone number, time constraints, billing information, etc. can be included.

In step 2, design centers: make models from imprints, if needed; use sensors to acquire digital shape information of patient's teeth from imprints and/or models, if needed; use sensors to acquire digital appearance information of patient's teeth in patient's mouth, if needed; and process this information to determine the desired results. This entails using the digital information regarding the shape and appearance of the patient's teeth as input for the CAD software to design and shape the appearance of the prosthesis so that the prosthesis fits the mouth of the patient and achieves an aesthetic appearance.

Design centers communicate desired results through Internet or modem line or other means of transmitting digital data to calculation centers along with complementary information to document cases and/or for transactional need. This information is similar to that described above, but may also include information to give specification that are outside the norm for a given process, requests for special care, and information related to the transaction between the design center and the supplier.

In step 3, calculation centers process this information to design how to achieve desired results and communicate how to achieve desired results through Internet or modem line or other means of transmitting digital data to manufacturing centers along with complementary information to document cases and/or for transactional need. The calculation center will select the most appropriate manufacturing process to obtain the desired result. Depending on the selected process, the calculation center provides the manufacturing center with the appropriate numerical data for carrying out the manufacturing.

For example, if a rapid-prototyping stereolithography process, such as the Cynovad WaxPro™ process, is selected, the calculation shall send a STL file. Another example would be the milling of a lithium disilicate reduced crown by a CNC machine. In this case, the calculation center would send an encapsulated tool paths file that describes the sequence of steps to mill the dental object with the different cutting tools along with the selected dental material identification number.

The calculation center also supplies a recipe to achieve the desired aesthetic qualities, e.g., the dental material identification number in the ring process example.

In step 4, manufacturing centers execute instructions to achieve desired results and send product to dental laboratory center. Regarding the manufacturing instructions, see, for example, Duret, U.S. Pat. Nos. 5,092,022, 4,742,464, 5,237,998, and 4,663,720; and Sjöln, European Patent Application No. 1 088 526. The inclusion of a set of instruction to achieve the desired aesthetic appearance is an additional feature of this step of the present invention.

Considering the examples noted above, if a rapid-prototyping stereolithography process, such as the Cynovad WaxPro™ process, is selected, the manufacturing center will receive a STL file. The STL file will serve as input to a rapid-prototyping stereolithography machine, such as 3D Systems' ThermoJet™ printer. A wax model will be produced and used to cast a precious-alloy coping.

If the milling process is selected, the manufacturing center shall receive an encapsulated tool paths file. The encapsulated tool paths file will serve as input to a CNC machine that was previously a blank of dental material corresponding to an identification number. The remaining instructions of the recipe are sent to the dental laboratory center.

Manufacturing centers communicate remaining instructions from the calculation center, if any, to achieve desired results through Internet or modem line or other means of transmitting digital data to manufacturing centers along with complementary information and/or for transactional need.

Step 5 consists in a skilled technician in the dental laboratory centers executing final instructions to achieve desired results and/or complete the prosthetic work, performing quality assurance procedures (installing the dental prostheses on the dental arch model to test the fit and/or to measure the appearance of the dental prostheses and check its correspondence with the desired appearance) sending final product to dentists, and communicating quality assurance data, if desired, to achieve desired results through Internet or modem line or other means of transmitting digital data to dentists along with complementary information to document cases and/or for transactional need. In addition to the complementary information described above, the dental lab could add explanations to justify any discrepancy between the final work and the desired appearance. Finally, dentists complete the dental procedures (step 6).

It is to be noted that, all communications between dentists, design centers, calculation centers, manufacturing centers and dental laboratory centers are preferably made via communication centers where the processes can be monitored and status reported to interested parties. Also, the communication centers are configured to select the best process center to distribute work given geographical constraints, resources availability and current workload.

The communication centers acquire knowledge on processes and use this technical and transactional knowledge to improve the processes, including among others technical and material improvements. By monitoring all of the transactions carried oat through the communication center network, including all defects. The communication center is thereby in a position to create a database for each of the process, for each dental material and establish statistically the appropriateness of a process or dental material in a given clinical situation. The communication centers also acquire a database of clinical cases, including both shape and appearance of teeth within a geographical segment. This knowledge can then be used in defining specifications for dental material, measuring devices, design tools and manufacturing processes.

Both design centers and manufacturing centers can also be installed at dental laboratories and/or dental offices. Dental technicians are the preferred users of design centers' CAD software tools for most major dental restoration procedures.

The design centers and manufacturing centers can have varying facilities according to the marketing decision with respect to perceived needs (e.g., a manufacturing unit for ceramic inlays such as the CEREC™ from SIRONA can be installed in a dental office; a manufacturing center can be specialized only in precious alloys).

According to a final aspect of the present invention, there is provided a method of communicating information related to dentistry and prosthesis.

More specifically, a system to Measure the Appearance of a Tooth (herein referred to as "MAT System") such as the ShadeScan System™ from Cortex Machina Corporation, can be seen, by the nature of the data it produces, as a means of communication between dental laboratories and dentists. Application specific portals centered around such a device can control and collect: transaction information; scientific information regarding natural teeth as well as marketing information ancillary to the system.

From this perspective, the e-commerce and e-products of an ASP based model revolving around a "MAT system" such as the ShadeScan System™ may take one of the following alternative or complementary forms: Pay-Per-Use or Pay-Per-Click business model.

According to this embodiment:
(a) The practitioner takes measurements of the patent's teeth by using a MAT system;
(b) A software included with the system maintains an historic database of the images and/or of the appearance maps, including the number of images, produced by the MAT system or the number of uses of the system accrued by the practitioner;
(c) The number of images and/or the images are then transmitted, either from the device itself or from a computer running the MAT system software, to a central server to be collated and integrated with the accounting information of the practitioner; and
(d) The practitioner then either receives a bill or has his account directly debited.

It is to be noted that the term "practitioner" as used in this application is intended to include dentists, dental assistants, dental technicians and any users in a dental office or in a dental laboratory.

Knowledge Information System (KS): According to this embodiment, a web-site collects and analyzes information of the MAT system transmitted between the dentists and dental laboratories to aid in the design and fabrication of dental prosthesis. To achieve this, the KIS uses collected shade guide information to build and design the appearance properties of the materials (both ceramic and composite materials) by advantageously, but not exclusively, using:
(i) The information to design the translucency scale for tooth restoration materials; and
(ii) The range, distribution and granularity of colors that define the keys of the shade guide and correspondingly the appearance properties of the elements composing the material systems that correspond to the shade guide. The design of a virtual shade guide that is self adapting as more information is accumulated.

The KIS also obtains information regarding the buying practices, services offered and internal procedures of both dentists and dental laboratories. This information could in turn be marketed externally as well have internal value, for example, to obtain information on the performance of tooth bleaching systems over time. The KIS nay also act as a clearinghouse where dental laboratories that desire a complete recipe would download the case information to a portal, for example, at the end of the business day. These requests are then entered into the clearinghouse where trained technicians can analyze them and determine the exact recipe to fabricate the restoration. This information may be verified and given an approval stamp by trained technicians before being passed back to the dental laboratory that can receive the information before the start of the next business day. A web site may advantageously follow one of these business models and apply it to digitize three-dimensional models of teeth.

Another form the system may take is an e-commerce service allowing for connecting the end-user with technicians specially trained in interpreting reports produced by the MAT, and to provide exact recipes to the client may be provided. The resulting knowledge that is accumulated may be analyzed to develop the following expert systems that are purely computer based: Resin recipe expert to provide expert software that will enable the dentist to quickly and accurately select the correct resin composite for partial tooth restoration and ceramic recipe expert to provide expert software that can advise the dental technician on the best ceramic recipe to use when fabricating replacement teeth and crowns.

Although the present invention has been described hereinabove by way of preferred embodiments thereof, it can be modified without departing from the spirit and nature of the subject invention, as defined in the appended claims. All of the above-identified patents and publications are hereby incorporated by reference in their entirety.

The invention claimed is:

1. A method to model dental restorations, said method comprising:
   (a) compiling a database of materials for use in preparing a dental restoration;
   (b) compiling a database of procedures for preparing said dental restoration;
   (c) determining the geometrical constraints of said dental restoration;
   (d) determining the aesthetic constraints of said dental restoration; and
   (e) inputting said geometrical constraints and said aesthetic constraints to a computer to mathematically select from said material database and said procedure database a recipe for producing said dental restoration; wherein said computer is further input with constraints determined by a dentist and/or dental technician, wherein said dentist and/or dental technician constraints comprise limitations on the choice of material, complexity of the procedure and/or coarseness of the recipe, and wherein said recipe coarseness is constrained by defining the minimal voxel size and/or limiting the number of sublayers.

2. A method as defined in claim 1 wherein said recipe is used as input to a machine for producing said dental restoration.

3. A method as defined in claim 2 wherein said machine comprises a milling machine, a plasma fusion machine or a rapid prototyping system.

4. A method as defined in claim 2 wherein said machine produces only part of said dental restoration and a person completes said recipe.

5. A method as defined in claim 2 further comprising using said produced dental restoration for validating said method.

6. A method as defined in claim 2 further comprising using said produced dental restoration for refining said method.

7. A method to model dental restorations, said method comprising:
   (a) compiling a database of materials for use in preparing a dental restoration;
   (b) compiling a database of procedures for preparing said dental restoration;
   (c) determining the geometrical constraints of said dental restoration;
   (d) determining the aesthetic constraints of said dental restoration; and
   (e) inputting said geometrical constraints and said aesthetic constraints to a computer to mathematically select from said material database and said procedure database a recipe for producing said dental restoration; wherein recipe selection comprises defining dental restoration and dividing said dental restoration volume into voxels and parameterizing each said voxel with one or more of absorption, diffusion, reflection, refraction and transmittance coefficients based on the wavelength of light entering said voxel.

8. A method as defined in claim 7 wherein said wavelength parameters are constrained to the human visual spectrum.

9. A method as defined in claim 7 wherein said dental restoration comprises a dental prosthesis.

10. A method as defined in claim 9 wherein said dental prosthesis is selected from the group consisting of a crown, a multiple-element prosthesis such as a bridge, a veneer, an inlay or an onlay.

11. A method as defined in claim 7 wherein said material database comprises material selections for use in one or more of a substructure, dentin, enamel, masks or stains.

12. A method as defined in claim 7 wherein said procedure database comprises one or more of a milling, plasma fusion, rapid-prototyping, layering and fusion of porcelain, polymerization of resins or composites.

13. A method as defined in claim 7 wherein said geometrical constraints are obtained from a theoretical teeth library, from a CAD system or both.

14. A method as defined in claim 13 wherein said CAD system obtains dental arcade shape information from a shape measuring device that uses optical means or a tactile system.

15. A method as defined in claim 7 wherein said aesthetic constraints are obtained from light reflection measurements.

16. A method as defined in claim 15 wherein said light reflection measurements comprises illuminating the teeth or dental restorations in a controlled way and measuring the light reflected from different regions of the teeth or dental restoration.

17. A method as defined in claim 16 wherein a color camera is used for measuring the reflected light.

18. A method as defined in claim 7 wherein said recipe for producing said dental restoration comprises a layer-by-layer instruction wherein each layer is characterized by its shape, thickness and material composition.

19. A method as defined in claim 18 wherein each layer may be divided into sublayers.

20. A method as defined in claim 7 wherein said computer is further input with constraints determined by a dentist and/or dental technician.

21. A method as defined in claim 20 wherein said dentist and/or dental technician constraints comprise limitations on the choice of material, complexity of the procedure and/or coarseness of the recipe.

22. A method for designing dental restoration with predetermined aesthetic qualities, said method comprising:
   (a) compiling a database of criteria for use in designing an aesthetic dental restoration;
   (b) compiling a database of procedures for preparing said dental restoration;
   (c) compiling a database of materials;
   (d) determining the geometrical constraints of said dental restoration;
   (e) determining the aesthetic constraints of said dental restoration; and
   (f) inputting said geometrical constraints and said aesthetic constraints to a computer to mathematically select from said criteria database, said procedure database and said material database a feasible design for said dental restoration using selected materials;
   (g) modeling dental restorations with said selected materials;
   (h) emulating said selected dental procedure with said selected material on said computer to image process the most likely outcome of the dental restoration
   wherein said dental restoration modeling includes the interaction of a light with said selected material, and wherein said interaction with a light with said selected material is computed for a sampling of wavelengths characteristic of human visual perception.

23. A method as defined in claim 22 further comprising comparing said predicted dental restoration image with the dental restoration to determine differences in morphology and/or symmetry.

24. A method as defined in claim 23 wherein said differences are input to said computer to build a database.

25. A method as defined in claim 23 wherein said selected dental procedure comprises a series of steps.

26. A method as defined in claim 25 wherein said differences are measured after each step in said selected dental restoration procedure.

27. A method as defined in claim 26 wherein said selected dental procedure comprises tooth whitening.

28. A method as defined in claim 27 wherein the appearance and shape of the tooth is measured before and after each tooth whitening application step.

29. A method for producing an aesthetic prosthesis, said method comprising:
(a) acquiring quantitative data on shape and appearance;
(b) processing said quantitative data to determine the desired result;
(c) further processing said quantitative data and the desired result to determine a method for achieving said desired result;
(d) manufacturing the underlying structure of said prosthesis; and
(e) finalizing said prosthetic work wherein said shape quantitative data and/or aesthetic quantitative data are communicated to a design center node.

30. A method as defined in claim 29 wherein said shape quantitative data comprises the digital measurement of teeth.

31. A method as defined in claim 30 wherein said shape quantitative data comprises is obtained by using sensors to acquire digital shape information of patient's teeth directly in the patient's mouth.

32. A method as defined in claim 30 wherein said shape quantitative data comprises taking an imprint of a patient's teeth; and using sensors to acquire digital shape information directly from said imprint or from a model prepared based on said imprint.

33. A method as defined in claim 29 wherein said appearance data comprises the digital measurement of the light reflection of the teeth.

34. A method as defined in claim 29 wherein said communication occurs through a computer network.

35. A method as defined in claim 34 wherein said computer network comprises the Internet.

36. A method as defined in claim 29 wherein said shape and aesthetic quantitative data are processed using computer aided design tool to determine the shape and appearance for said prosthesis.

37. A method as defined in claim 36 wherein said shape and appearance for said prosthesis is communicated to a calculation center node.

38. A method as defined in claim 37 wherein said communication occurs through a computer network.

39. A method as defined in claim 38 wherein said computer network comprises the Internet.

40. A method as defined in claim 29 wherein said shape and aesthetic quantitative data are received by a computer aided design tool from said design center node to determine the shape and appearance for said prosthesis.

41. A method as defined in claim 29 wherein said desired shape and appearance for said prosthesis information is further processed to determine a method for achieving said desired result using computer aid manufacturing tools to determine the manufacturing process for manufacturing the underlying structure of the prosthesis and the steps required for finishing the prosthesis.

42. A method as defined in claim 41 wherein said manufacturing process is communicated to a production center node.

43. A method as defined in claim 42 wherein said communication occurs through a computer network.

44. A method as defined in claim 43 wherein said computer network comprises the Internet.

45. A method as defined in claim 29 wherein said manufacturing comprises milling, rapid prototyping or deposition on model to produce said underlying structure for said prosthesis.

46. A method as defined in claim 45 wherein said underlying structure for said prosthesis and finishing instructions are forwarded to a dental laboratory node.

47. A method as defined in claim 29, wherein said communications to said design center node, calculation center node, production center node, and dental laboratory node are made through a communication center.

48. A method as defined in claim 47 wherein said communication center uses the data from said communications to develop a database of clinical cases.

49. A method for communicating information related to dentistry comprising;
(a) collecting information regarding a dentistry procedure;
(b) communicating said information to a central source via a computer network for analysis, wherein the information received by said central source is analyzed to determine a recipe for fabricating a dental restoration;
wherein said collected information comprises transactional information, scientific information regarding natural teeth, marketing information and combinations thereof.

50. A method as defined in claim 49 wherein said scientific information regarding natural teeth comprises shape measurements.

51. A method as defined in claim 49 wherein a tooth appearance measurement device is used to collect said information.

52. A method as defined in claim 51 wherein said information from the tooth appearance measurement device is communicated to a web site via the internet.

53. A method as defined in claim 52 wherein the information received by said web site is analyzed to collect shade guide information to design a translucency scale for tooth restoration materials.

54. A method as defined in claim 53 wherein the information received by said web site is analyzed to determine the range, distribution and granularity of colors for tooth restoration material systems.

55. A method as defined in claim 49 wherein (i) a practitioner takes measurements and/or images of a patient's teeth using a tooth appearance measurement device; (ii) said device includes software for maintaining an historic database of said measurements and/or images; (iii) said device communicates said measurements and/or images to a central server; (iv) the central server collates and integrates the received measurements and/or images with accounting information regarding the practitioner; and (v) the central server generates a bill to the practitioner or directly debits the practitioner's account.

56. A method as defined in claim 49 wherein said transactional and marketing information is analyzed to obtain information regarding buying practices, services offered and/or internal procedures of dentists and dental laboratories.

57. A method as defined in claim 49 further comprising collecting said recipes in a database to develop an expert resin recipe database and/or an expert ceramic recipe database.

* * * * *